(12) United States Patent
Fosse et al.

(10) Patent No.: US 10,384,058 B2
(45) Date of Patent: Aug. 20, 2019

(54) METHODS AND DEVICES FOR SECURING A SENSOR AT THE HEART

(71) Applicant: Cardiaccs AS, Oslo (NO)

(72) Inventors: Erik Fosse, Oslo (NO); Jonas Tyssø, Oslo (NO)

(73) Assignee: Cardiaccs AS, Oslo (NO)

(*) Notice: Subject to any disclaimer, the term of this patent is extended or adjusted under 35 U.S.C. 154(b) by 0 days.

(21) Appl. No.: 16/008,830

(22) Filed: Jun. 14, 2018

(65) Prior Publication Data

US 2018/0361141 A1    Dec. 20, 2018

(30) Foreign Application Priority Data

Jun. 16, 2017  (GB) .................................. 1709621.5

(51) Int. Cl.
| A61N 1/05 | (2006.01) |
| A61B 5/042 | (2006.01) |
| A61N 1/37 | (2006.01) |
| A61B 5/00 | (2006.01) |
| A61B 5/0408 | (2006.01) |

(Continued)

(52) U.S. Cl.
CPC ............ *A61N 1/059* (2013.01); *A61B 5/0408* (2013.01); *A61B 5/6882* (2013.01); *A61N 1/0595* (2013.01); *A61N 1/36578* (2013.01); *A61N 1/37* (2013.01); *A61B 5/1107* (2013.01);

(Continued)

(58) Field of Classification Search
CPC ..... A61N 1/0592; A61N 1/059; A61N 1/0595
See application file for complete search history.

(56) References Cited

U.S. PATENT DOCUMENTS 4,414,986 A * 11/1983 Dickhudt ............... A61N 1/057
607/117
4,437,475 A * 3/1984 White .................... A61N 1/056
607/126

(Continued)

FOREIGN PATENT DOCUMENTS

EP    0 211 166 B2    2/1987
EP    0 655 260 A2    5/1995

(Continued)

OTHER PUBLICATIONS

Examination Report directed to European Patent Application No. GB1709621.5, dated Oct. 23, 2018; 2 pages.

(Continued)

*Primary Examiner* — Kennedy Schaetzle
(74) *Attorney, Agent, or Firm* — Sterne, Kessler, Goldstein & Fox P.L.L.C.

(57) ABSTRACT

An apparatus for securing a sensor at the heart is formed based on a modified, branched, pacemaker lead to provide a heart anchor lead where two anchors are coupled to a single main lead rather than there being just a single anchor. Thus, the proposed heart anchor lead comprises a single main lead, a sensor included within the main lead, in which the sensor has a distal end and a proximal end, a first anchor coupled to the distal end of the sensor and extending outward from the distal end of the sensor, and a second anchor coupled to the proximal end of the sensor and extending outward from the proximal end of the sensor in a direction that forms an angle with the first anchor. The heart anchor lead can optionally also have a pacemaking function.

18 Claims, 12 Drawing Sheets

(51) Int. Cl.
*A61N 1/365* (2006.01)
*A61B 5/11* (2006.01)

(52) U.S. Cl.
CPC ............ *A61B 5/6869* (2013.01); *A61N 1/0592* (2013.01); *A61N 1/36542* (2013.01)

(56) References Cited

U.S. PATENT DOCUMENTS

| | | | |
|---|---|---|---|
| 4,967,755 A * | 11/1990 | Pohndorf | A61N 1/056 600/488 |
| 5,031,615 A | 7/1991 | Alt | |
| 5,350,419 A * | 9/1994 | Bendel | A61N 1/05 600/374 |
| 5,353,800 A * | 10/1994 | Pohndorf | A61B 5/0215 600/486 |
| 5,376,108 A * | 12/1994 | Collins | A61N 1/056 604/174 |
| 5,476,500 A * | 12/1995 | Fain | A61N 1/0563 600/375 |
| 5,609,612 A | 3/1997 | Plicchi et al. | |
| 6,221,024 B1 * | 4/2001 | Miesel | A61B 5/0215 600/486 |
| 6,434,431 B1 | 8/2002 | Camps et al. | |
| 6,658,292 B2 | 12/2003 | Kroll et al. | |
| 6,937,899 B2 * | 8/2005 | Sheldon | A61B 5/04011 600/513 |
| 7,200,437 B1 | 4/2007 | Nabutovsky et al. | |
| 7,203,551 B2 * | 4/2007 | Houben | A61N 1/08 310/366 |
| 8,311,645 B2 * | 11/2012 | Bolea | A61N 1/0556 607/118 |
| 8,632,473 B2 | 1/2014 | Sowelam | |
| 8,644,927 B2 | 2/2014 | Imran | |
| 8,731,662 B2 | 5/2014 | Imran | |
| 8,744,572 B1 | 6/2014 | Greenhut et al. | |
| 9,078,581 B2 * | 7/2015 | Osypka | A61B 5/042 |
| 9,138,160 B2 | 9/2015 | Imran | |
| 9,211,415 B2 | 12/2015 | Saha et al. | |
| 9,247,883 B2 | 2/2016 | Sowelam | |
| 9,764,142 B2 | 9/2017 | Imran | |
| 2003/0105496 A1 | 6/2003 | Yu et al. | |
| 2006/0020317 A1 * | 1/2006 | Flach | A61N 1/0573 607/130 |
| 2006/0178589 A1 | 8/2006 | Dobak, III | |
| 2007/0255295 A1 | 11/2007 | Starkebaum et al. | |
| 2008/0281214 A1 | 11/2008 | Elle et al. | |
| 2010/0137949 A1 * | 6/2010 | Mazgalev | A61N 1/0587 607/72 |
| 2011/0224655 A1 * | 9/2011 | Asirvatham | A61M 1/1072 606/1 |
| 2012/0095521 A1 | 4/2012 | Hintz | |
| 2014/0207202 A1 | 7/2014 | Imran | |
| 2014/0236033 A1 | 8/2014 | Imran | |
| 2014/0243593 A1 | 8/2014 | Goode et al. | |
| 2016/0022998 A1 | 1/2016 | Imran | |

FOREIGN PATENT DOCUMENTS

| | | |
|---|---|---|
| EP | 1 458 290 B1 | 4/2009 |
| EP | 2 198 916 A1 | 6/2010 |
| EP | 2 421 607 B1 | 2/2012 |
| EP | 2 478 935 B1 | 7/2012 |
| EP | 2 703 041 B1 | 3/2014 |
| WO | WO 2005/039690 A1 | 5/2005 |
| WO | WO 2010/123895 A2 | 10/2010 |
| WO | WO 2011/002546 A1 | 1/2011 |
| WO | WO 2012/154599 A2 | 11/2012 |
| WO | WO 2015/172023 A2 | 11/2015 |
| WO | WO 2015/172023 A3 | 11/2015 |
| WO | WO 2016/118814 A1 | 7/2016 |
| WO | WO 2016/201082 A1 | 12/2016 |
| WO | WO 2018/142186 A1 | 8/2018 |

OTHER PUBLICATIONS

International Search Report dated Dec. 15, 2017 for Appl. No. GB1709621.5, 5 pages.
International Search Report and Written Opinion directed to International Appl. No. PCT/IB2018/054432, dated Oct. 26, 2018; 14 pages.

* cited by examiner

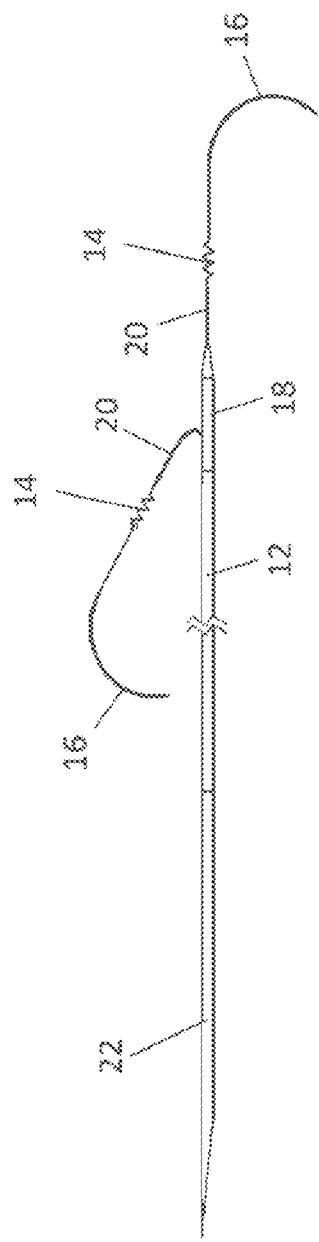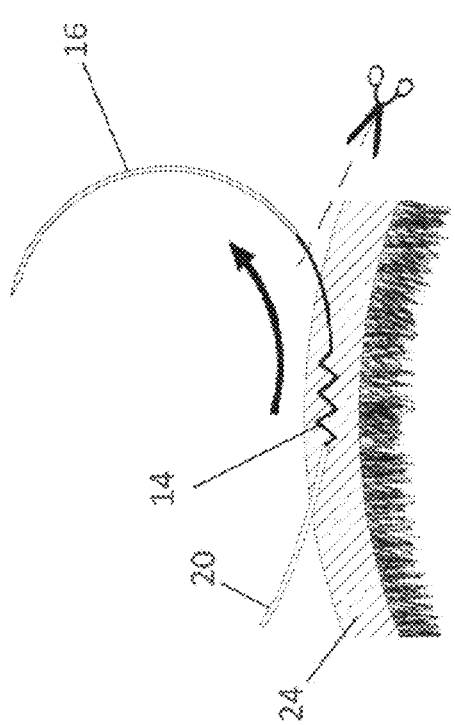

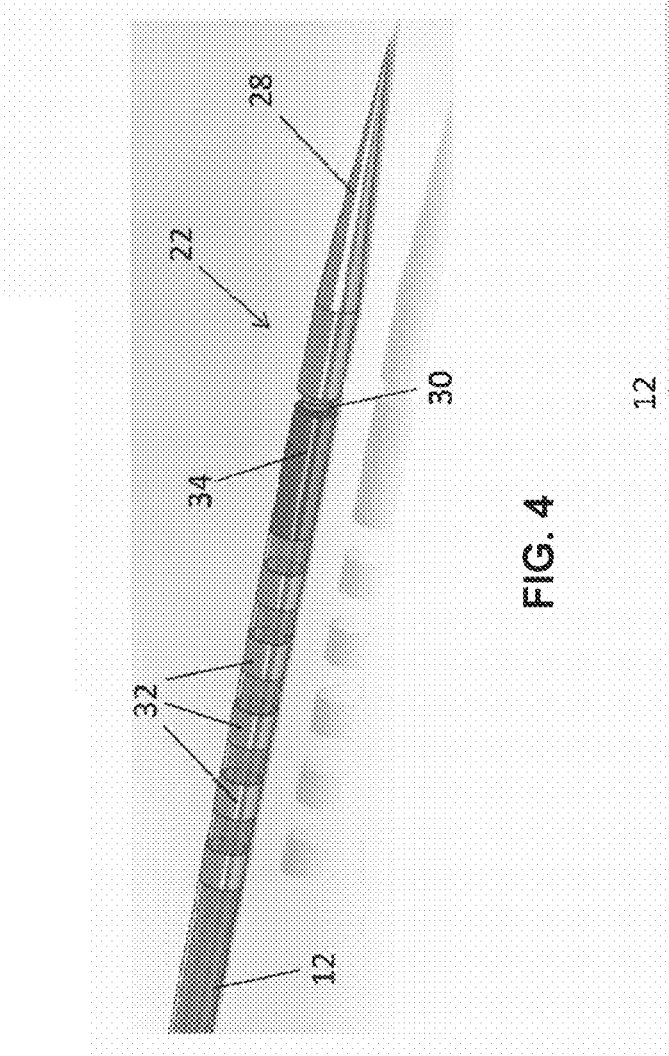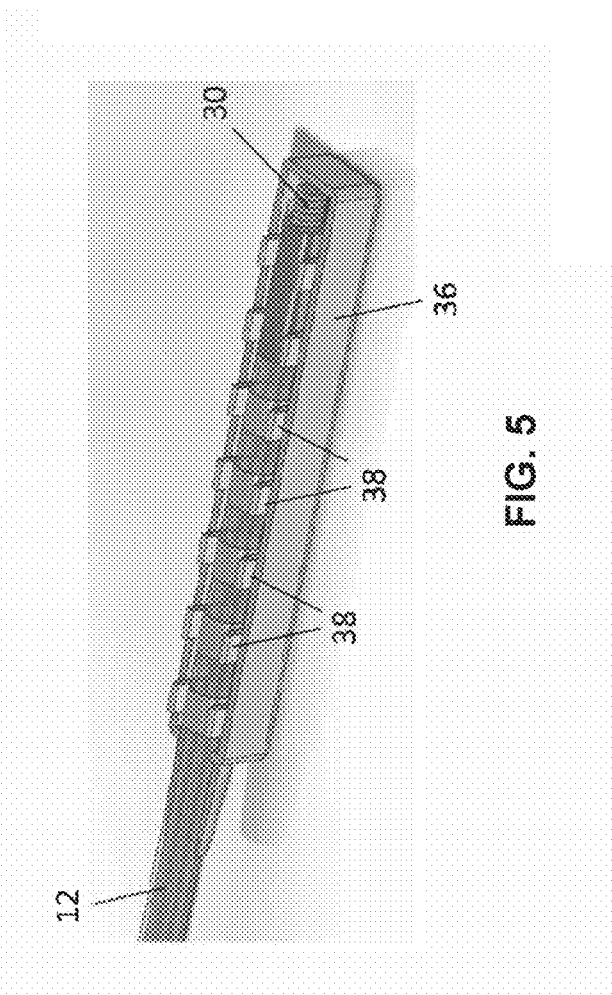
FIG. 4
FIG. 5

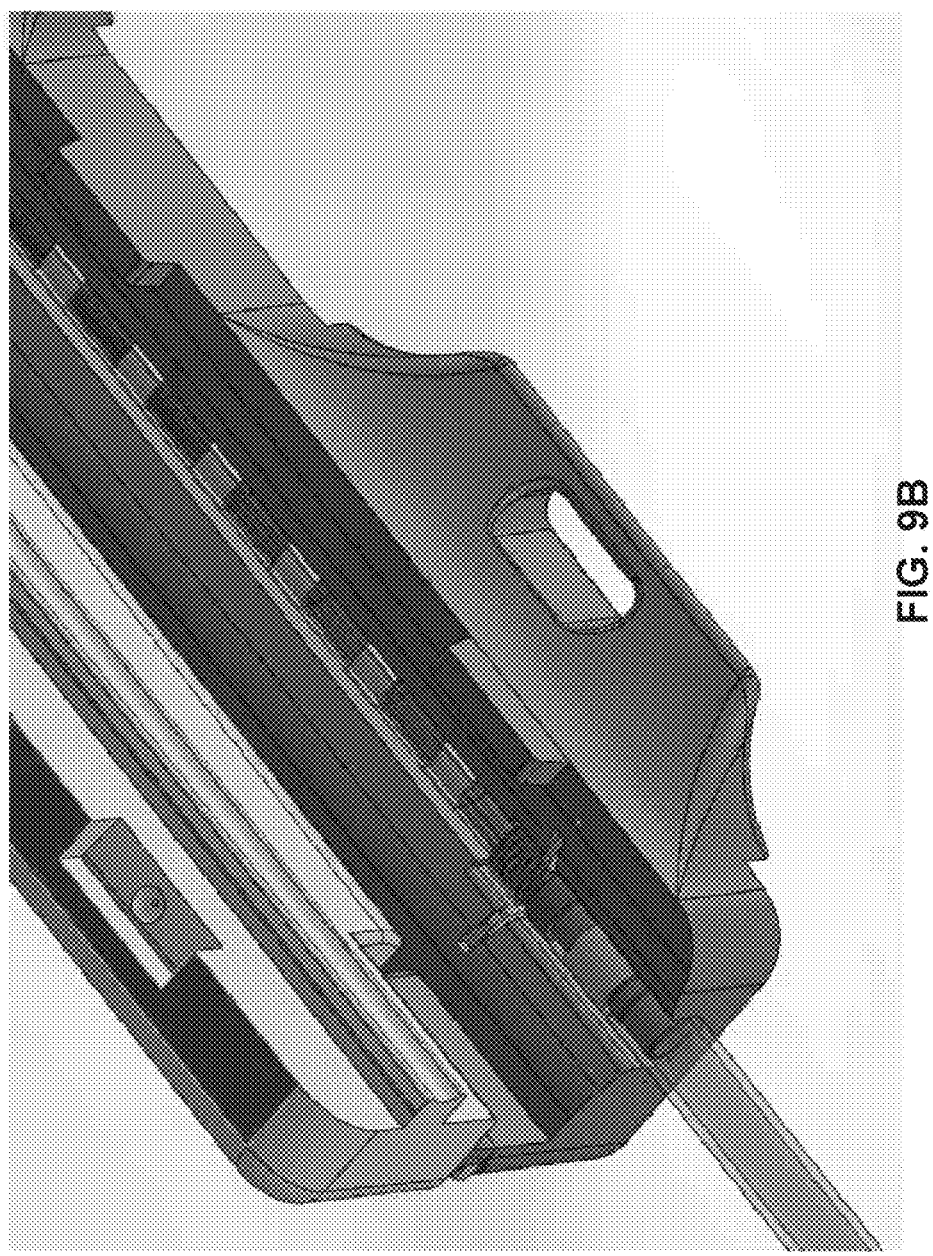

METHODS AND DEVICES FOR SECURING A SENSOR AT THE HEART

CROSS-REFERENCE TO RELATED APPLICATIONS

This application claims the benefit of United Kingdom Application No. GB 1709621.5, filed on Jun. 16, 2017, which is incorporated by reference herein in its entirety.

BACKGROUND OF THE INVENTION

Field of the Invention

The present invention relates to an apparatus and a method for securing a sensor at the heart and to a related system for monitoring the heart.

Background Art

It is often desirable to monitor the functioning of the heart and/or medical devices related to the heart, such as pacemakers and cardiac assist devices. However, a need exists for new methods and devices for effectively stabilizing a sensor for heart monitoring.

BRIEF SUMMARY OF THE INVENTION

Example methods, apparatuses, and systems are described herein for securing a sensor to a heart of a patient and monitoring the patient's heart.

In an embodiment, an apparatus for securing a sensor to a heart of a patient includes a heart anchor lead having a main lead, a sensor included within the main lead, the sensor having a distal end and a proximal end, a first anchor coupled to the distal end of the sensor and extending outward from the distal end of the sensor, and a second anchor coupled to the proximal end of the sensor and extending outward from the proximal end of the sensor in a direction that forms an angle with the first anchor.

In another embodiment, a heart monitoring system for monitoring a patient's heart is described. The heart monitoring system includes a sensing device and a data processing apparatus. The sensing device includes a heart anchor lead having a main lead, a sensor included within the main lead, the sensor having a distal end and a proximal end, a first anchor coupled to the distal end of the sensor and extending outward from the distal end of the sensor, a second anchor coupled to the proximal end of the sensor and extending outward from the proximal end of the sensor in a direction that forms an angle with the first anchor. The data processing apparatus is coupled to the sensing device and configured to receive motion sensor data from the sensing device.

In yet another embodiment, method for securing a sensing device to a heart of a patient is described. The method includes providing a sensing device for monitoring the patient's heart, in which the sensing device includes a heart anchor having a main lead, a sensor included within the main lead, a first anchor, and a second anchor, the sensor having a distal end and a proximal end. The method further includes attaching the first and second anchors to a left ventricle of the heart, and securing the sensor to a surface of the heart.

Further features and advantages, as well as the structure and operation of various embodiments, are described in detail below with reference to the accompanying drawings.

It is noted that the specific embodiments described herein are not intended to be limiting. Such embodiments are presented herein for illustrative purposes only. Additional embodiments will be apparent to persons skilled in the relevant art(s) based on the teachings contained herein.

BRIEF DESCRIPTION OF THE DRAWINGS/FIGURES

The accompanying drawings, which are incorporated herein and form a part of the specification, illustrate embodiments of the present disclosure and, together with the description, further serve to explain the principles of the disclosure and to enable a person skilled in the pertinent art to make and use the embodiments.

FIG. 1 illustrates an example diagram of a heart anchor lead for securing a sensor to the heart, according to an embodiment of the present disclosure.

FIG. 2 illustrates an example diagram of an anchor of the heart anchor lead being implanted into the myocardium using a curved needle, according to an embodiment of the present disclosure.

FIG. 4 illustrates an example diagram of a connector at a proximal end of the lead, according to an embodiment of the present disclosure.

FIG. 5 illustrates an example diagram of a connector coupled to an adaptor, according to an embodiment of the present disclosure.

Figure 8A:
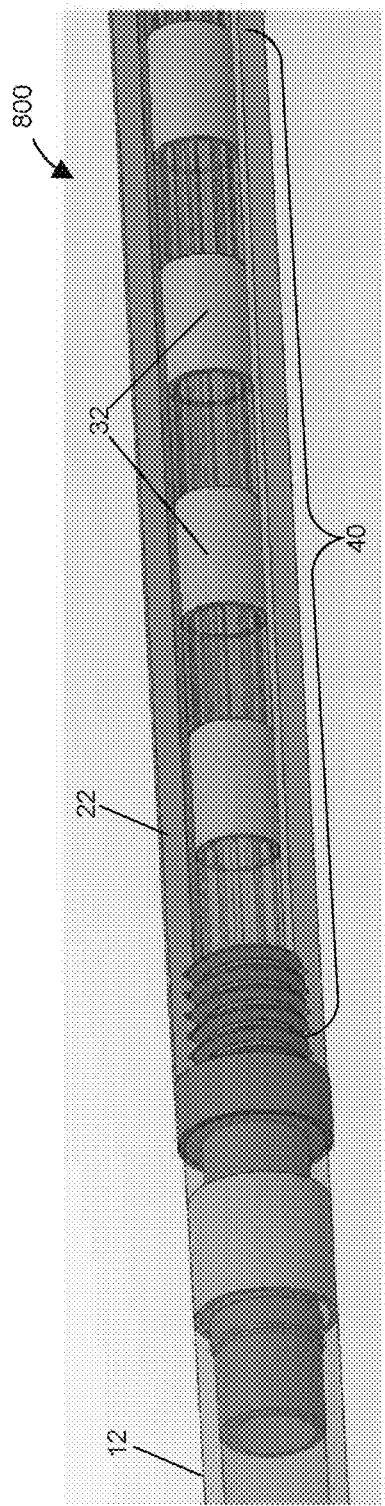
Figure 8B:
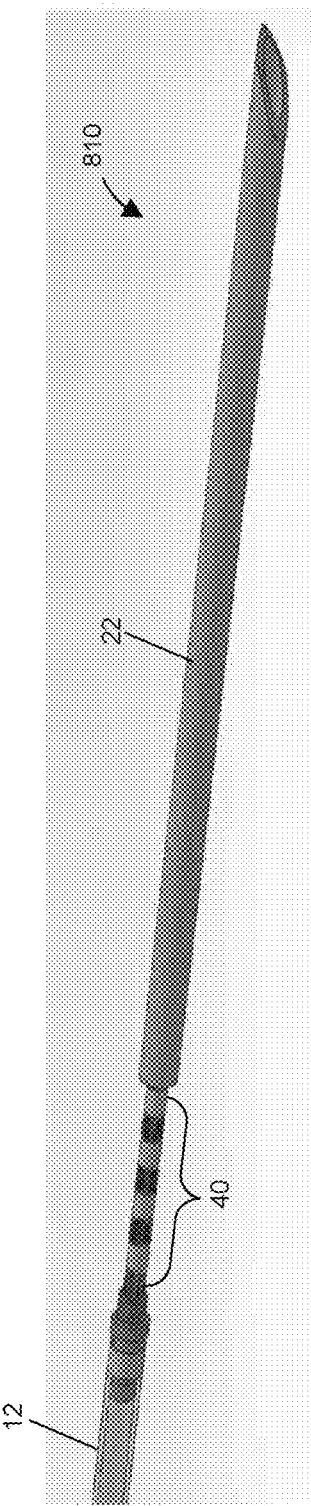
Figure 8C:
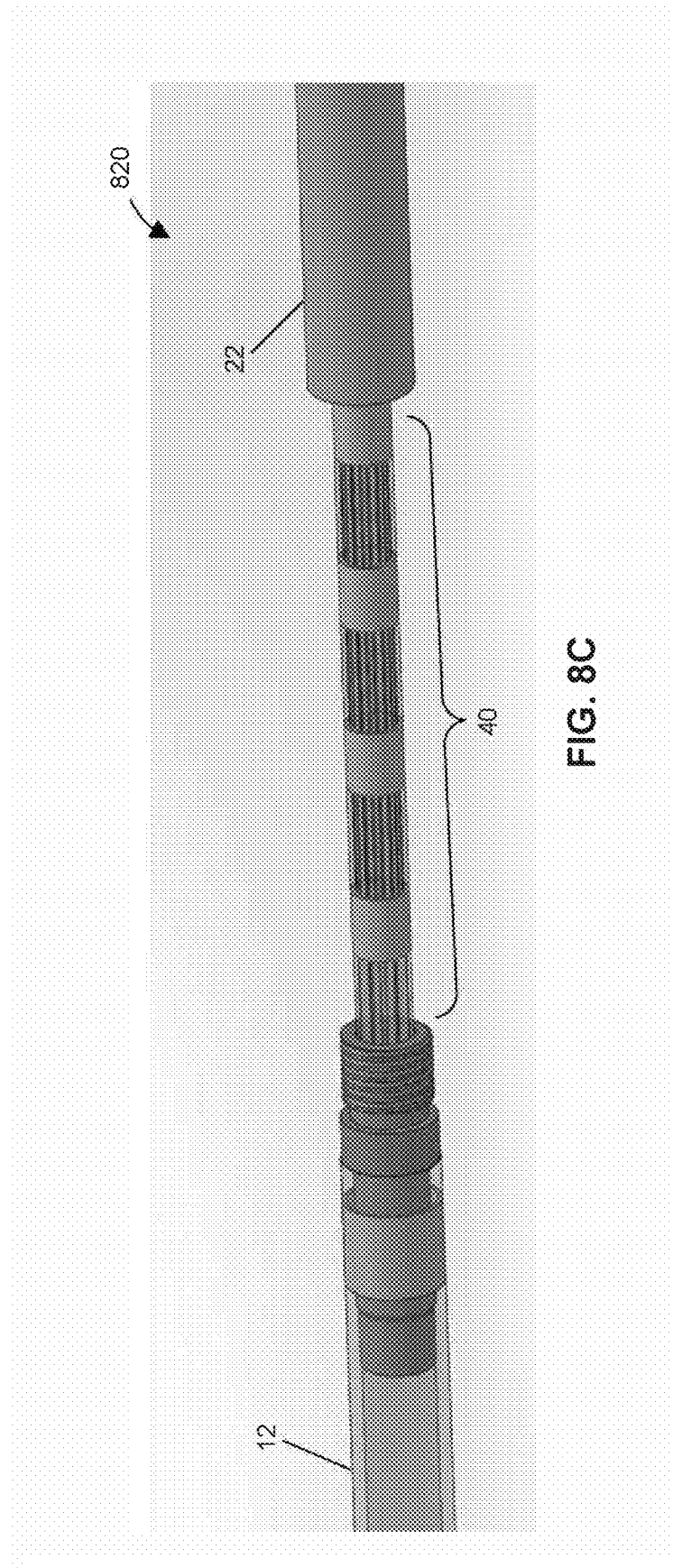

FIGS. 8A, 8B, and 8C illustrate example diagrams of a connector that is configured for placement within a needle, according to an embodiment of the present disclosure.

Figure 9A:
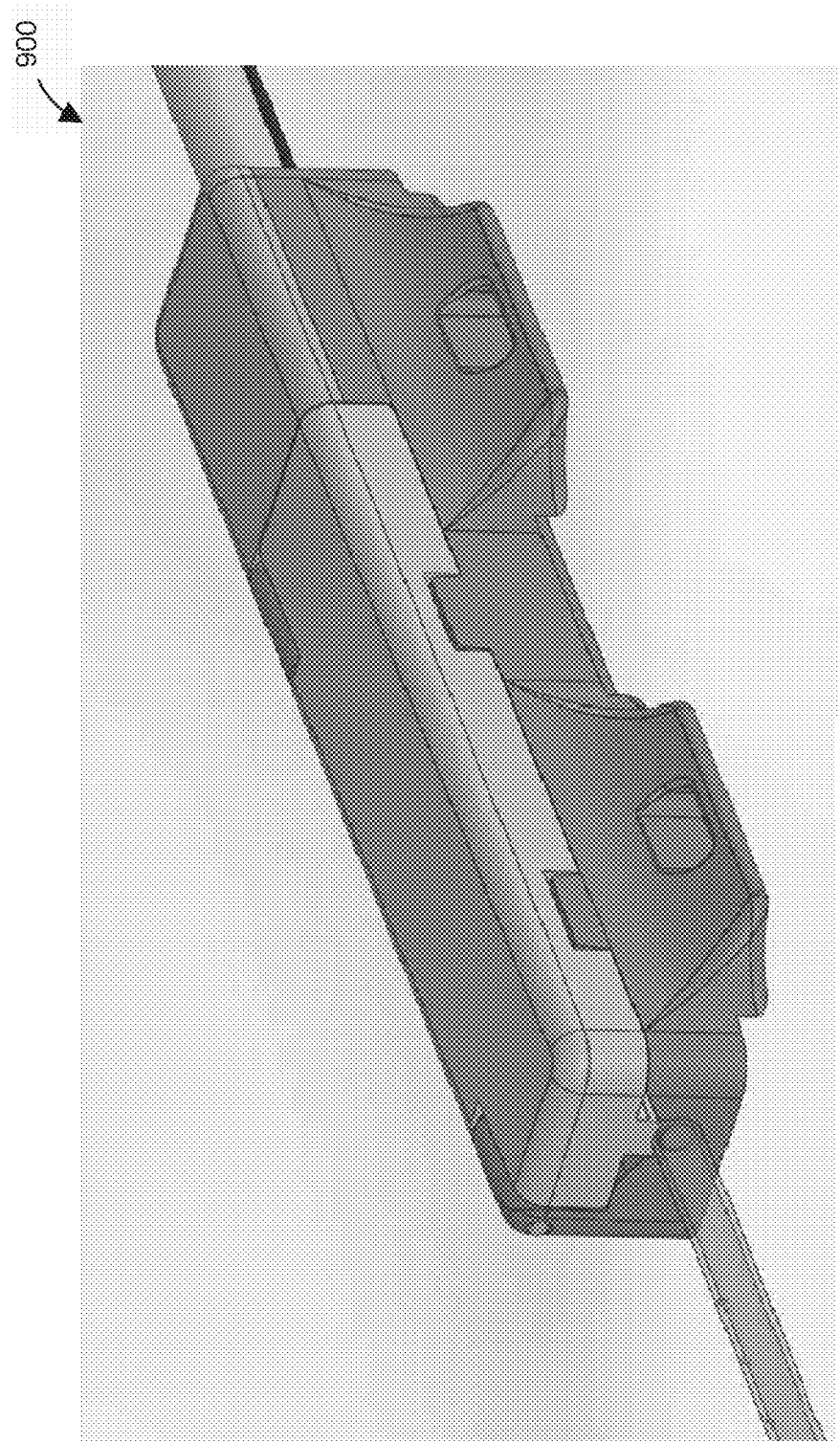
Figure 9C:
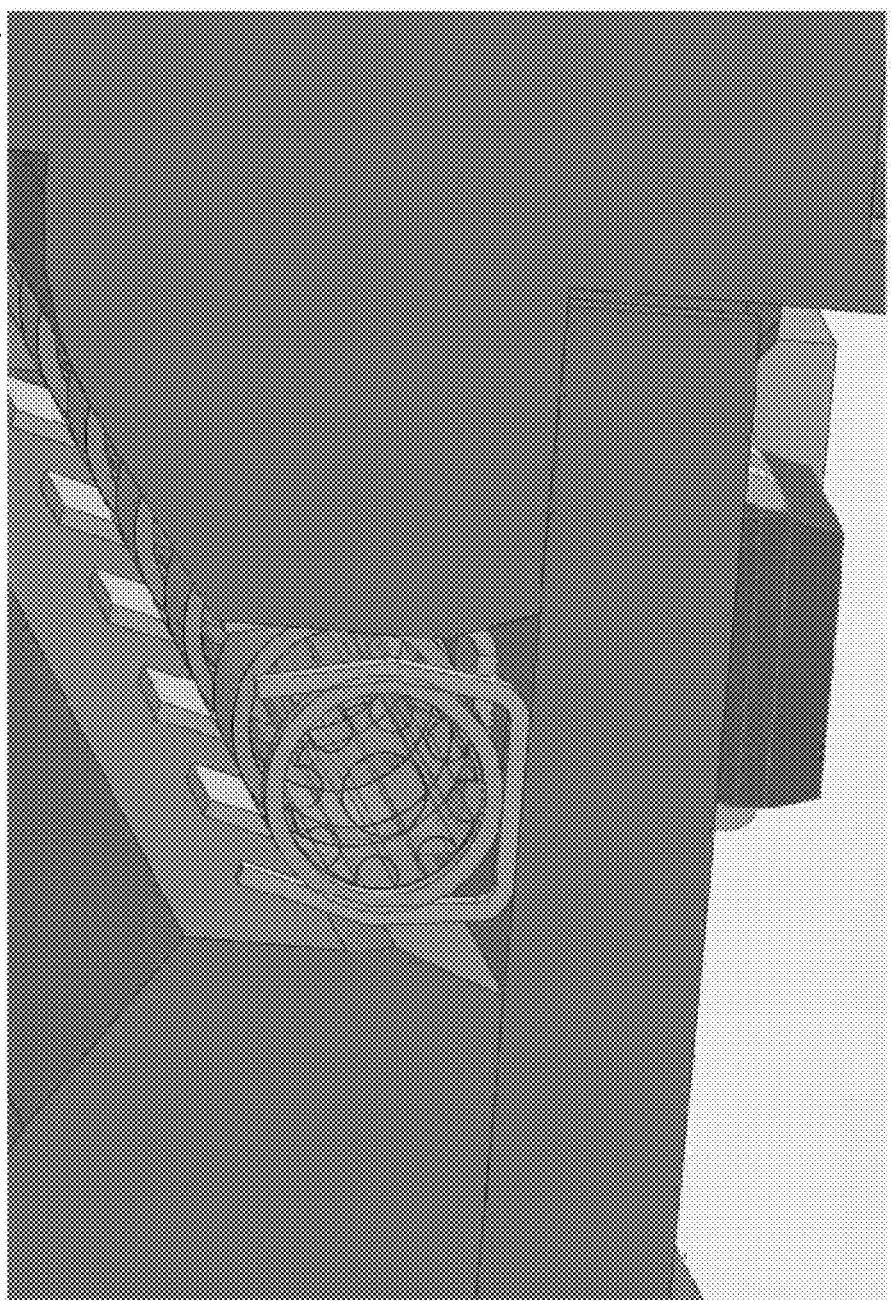

FIGS. 9A, 9B, and 9C illustrate example diagrams of a connector coupled to an adaptor, according to an embodiment of the present disclosure.

Figure 10:
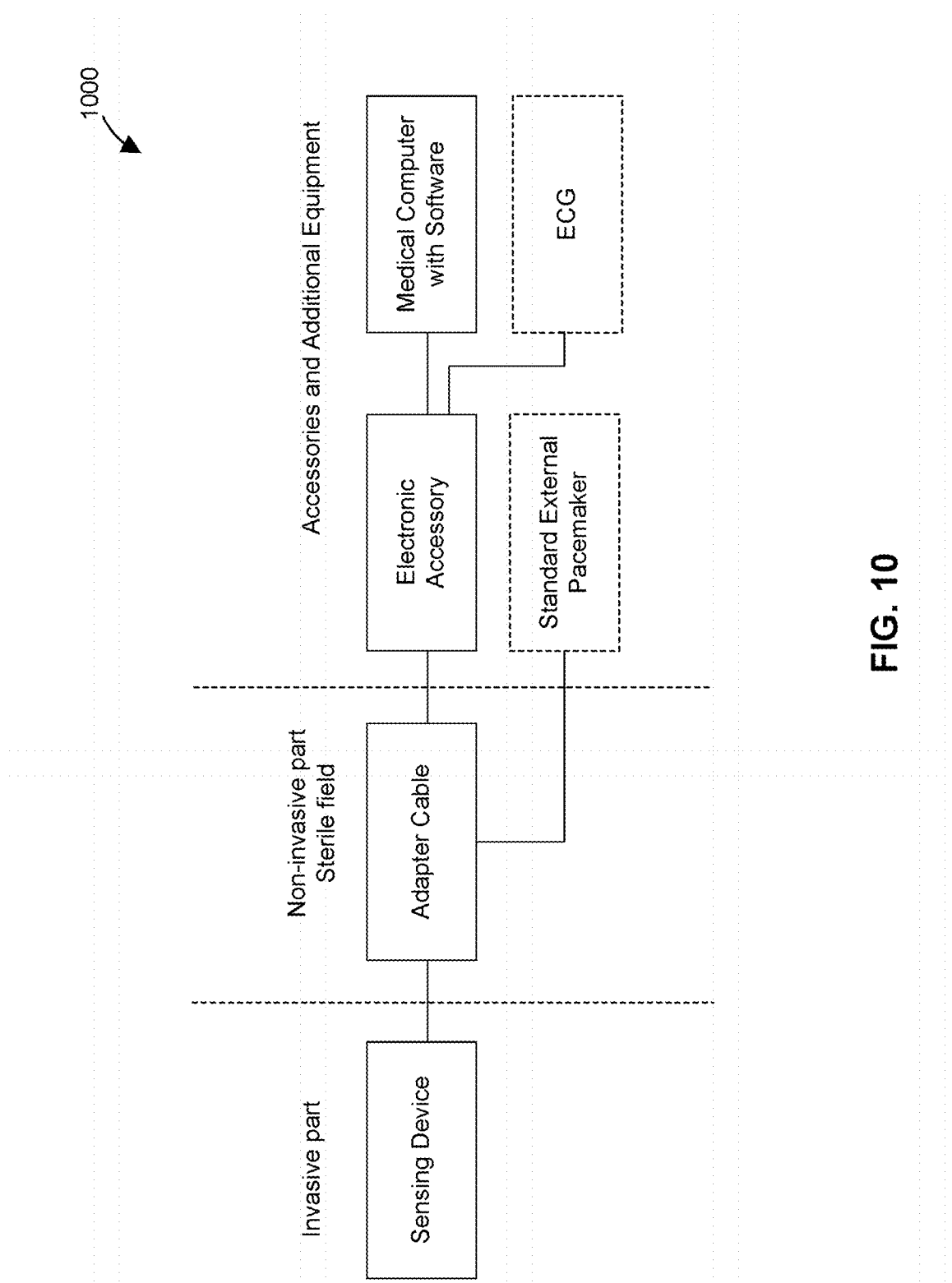

FIG. 10 illustrates an example block diagram of an environment of a sensing device coupled to other components for heart function assessment, according to an embodiment of the present disclosure.

Figure 11:
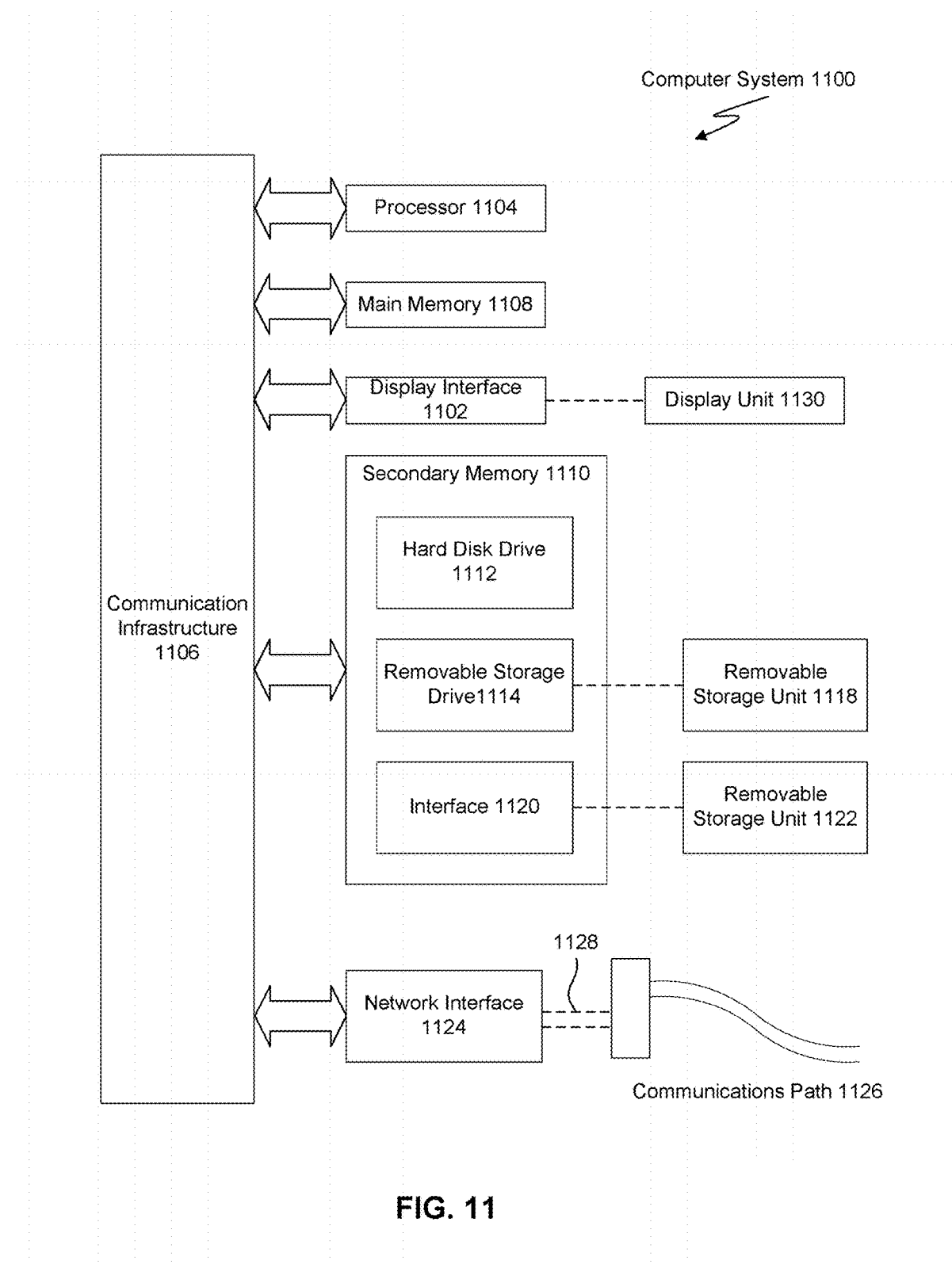

FIG. 11 illustrates an example computer system, according to an embodiment of the present disclosure.

The present disclosure will be described with reference to the accompanying drawings. In the drawings, like reference numbers indicate identical or functionally similar elements. Additionally, the left most digit(s) of a reference number identifies the drawing in which the reference number first appears.

DETAILED DESCRIPTION OF THE INVENTION

The following Detailed Description refers to accompanying drawings to illustrate exemplary embodiments consistent with the disclosure. References in the Detailed Description to "one exemplary embodiment," "an exemplary embodiment," "an example exemplary embodiment," etc., indicate that the exemplary embodiment described may include a particular feature, structure, or characteristic, but every exemplary embodiment may not necessarily include the particular feature, structure, or characteristic. Moreover, such phrases are not necessarily referring to the same exemplary embodiment. Further, when a particular feature, structure, or characteristic is described in connection with an exemplary embodiment, it is within the knowledge of those skilled in the relevant art(s) to affect such feature, structure, or characteristic in connection with other exemplary embodiments whether or not explicitly described.

The exemplary embodiments described herein are provided for illustrative purposes, and are not limiting. Other exemplary embodiments are possible, and modifications may be made to the exemplary embodiments within the spirit and scope of the disclosure. Therefore, the Detailed Description is not meant to limit the invention. Rather, the scope of the invention is defined only in accordance with the following claims and their equivalents.

The following Detailed Description of the exemplary embodiments will so fully reveal the general nature of the invention that others can, by applying knowledge of those skilled in relevant art(s), readily modify and/or adapt for various applications such exemplary embodiments, without undue experimentation, without departing from the spirit and scope of the disclosure. Therefore, such adaptations and modifications are intended to be within the meaning and plurality of equivalents of the exemplary embodiments based upon the teaching and guidance presented herein. It is to be understood that the phraseology or terminology herein is for the purpose of description and not of limitation, such that the terminology or phraseology of the present specification is to be interpreted by those skilled in relevant art(s) in light of the teachings herein.

It is often desirable to monitor the functioning of the heart and/or medical devices related to the heart, such as pacemakers and cardiac assist devices. In the prior art, various proposals have been made for ways to more effectively monitor a patient in this way. EP describes a motion sensor for registering movements of the surface of the heart. The sensor in this case can be a three axis accelerometer. It is designed to be temporarily implanted for monitoring a patient's heart before, during and/or after a surgical operation, for example to monitor for ischemia. U.S. Pat. No. 8,282,568 describes a system that uses data recorded by an accelerometer positioned on an outer surface of the heart for estimating changes in cardiac pumping capacity in response to an intervention. WO 2014/207225 describes the use of an accelerometer implanted at the heart or at a cardiac assist device such as an implanted pump. As set out in in WO 2014/207225, a motion sensor at the heart, such as an accelerometer, can be used to find information about the function of the cardiac assist device as well as information about the function of the heart.

Sensing the motion of the heart can be used in combination with or in place of conventional monitoring using ECG or other heart monitoring techniques and it is considered to provide advantages in relation to the accuracy of the information that is provided in relation to heart function. When the heart is monitored using a motion sensor such as an accelerometer it is necessary to secure the sensor at the heart. Typically this is done by a surgical procedure to implant the sensor. EP 1458290 suggests that an accelerometer may be temporarily affixed to the heart beneath the epicardium using surgical sutures or via a pacemaker lead.

Pacemaker leads have been known for some time, for example as described in WO 97/25099.

Temporary pacemaker leads typically comprise a curved cardiac needle for hooking into the myocardium; an anchor connected to the cardiac needle and arranged to anchor the pacemaker lead in the myocardium; a pacemaker electrode connected to the anchor; a main lead connected to the pacemaker electrode; and a thorax needle at the end of the main lead. The cardiac needle is passed through the myocardium and then anchor is then pulled through the myocardium. The anchor retains the pacemaker electrode in the desired position in the myocardial tissue after the cardiac needle is removed. In WO 97/25099 the anchor is a helix (or 'pigtail') formed in a wire. It is also known to use other shapes within the wire, such as a zig-zag wire. Using a shape formed in a wire allows the anchor to easily connect to the curved needle via a continuation of the wire. The pacemaker electrode includes an exposed conductive material, such as platinum or similar, and this can be an extension of the wire of the anchor. The main lead is an insulated wire for extending from the pacemaker electrode to the outside of the body where it can be electrically connected to a control apparatus, and the wire of the main lead can be a continuation of the wire of the anchor and the electrode in some cases. The thorax needle can be a straight or a curved needle and it is used for puncturing the chest wall from the inside so that the main lead can be pulled through. The thorax needle is removed after the pacemaker lead has been implanted, in order to allow connection to the control apparatus.

The invention of EP 1458290 provided a significant advance in the field of heart monitoring by allowing for an accelerometer to be directly located on the heart wall by means of a pacemaker type lead. Having an accelerometer small enough to be placed beneath the epicardium in a similar fashion to a pacemaker electrode allows for accurate monitoring of the heart using motion sensing to directly obtain measurements of heart movement. This can be implanted using relatively routine techniques that have been well-established for pacemaker leads.

Viewed from a first aspect, the present disclosure provides an apparatus for securing a sensor at the heart, the apparatus comprising: a heart anchor lead having a single main lead; a first anchor coupled to the main lead and extending from a branch point; a second anchor coupled to the main lead and extending from the branch point; and a sensor fixed to the apparatus at a point between the main lead and one or both of the anchors.

This apparatus may be considered as using a modified, branched, pacemaker lead to provide a heart anchor lead where two anchors are coupled to a single main lead rather than there being just a single anchor. The heart anchor lead can hence take a branched form such as Y-shape or a T-shape. It has been found that with the use of a conventional pacemaker lead as in EP 1458290 then the sensor may twist during movement of the heart and/or during movement of the patient's body. The sensor may also slide or shift along the surface of the heart, for example in cases where the surgeon was unable to fully secure the sensor with the anchor of the pacemaker lead. Since the sensor of EP 1458290 is a motion sensor, such as an accelerometer, then movements of the sensor create inaccuracies and increased noise in the sensor readings. By adding a second anchor then the sensor can be more effectively held with minimal movement relative to the myocardium. This allows for better measurements of the movement of the heart, which in turn allows for better assessment of the function of the heart as well as the function of other sources of movement, such as a cardiac assist device that can generate vibrations and other movements at the heart.

The sensor may be a motion sensor and in example embodiments an accelerometer is used. Accelerometers are readily available with a sufficient level of accuracy and a required small size to be implanted at the heart. This could for example be a three-axis accelerometer for obtaining measurements of three dimensional heart movements, although other types of accelerometer may also be used. Suitable sensors include MEMS tri-axis accelerometers and gyroscopes, for example. For example, a gyroscope may be utilized to measure angular velocity of the heart and obtain measurements indicating abnormal heart motion. In some embodiments, the sensor may include an accelerometer and a gyroscope for measuring heart motion.

The proposed apparatus may not have any pacemaker function and thus it may act purely as a heart anchor lead to hold the sensor at the heart. However, it is considered to provide advantages if the apparatus can both secure the sensor to the heart and also allow for one or two pacemaker electrodes to also be fixed to the myocardium. Thus, the heart anchor lead may be seen as a modified pacemaker lead with one or two pacemaker electrodes between the main lead and one or both of the anchors. In this case then one or both of the anchors may be coupled to the branch point by a wire that acts as a pacemaker electrode. This means that the pacemaker electrode is at the distal end of the lead, after the branch point, and where both branches of the lead have pacemaker electrodes then the two electrodes can be implanted into the heart at separate locations by pulling the branched structure of the apparatus open, such as in a Y-shape. Moreover, since pacing requires two electrodes through a bipolar pacemaker, or one pacemaker electrode and a further electrode somewhere else on the body, then by using both branches of the heart anchor lead to also provide pacemaker electrodes then this provides the benefit of not requiring a second pacemaker lead, or a further electrode placed elsewhere.

The sensor is located between the main lead and one or both anchors. Typically the sensor will be close to the branch point, and it may be located at the branch point. The sensor may thus be located in a similar position between an anchor and the main lead to the pacemaker electrode in a conventional pacemaker lead. The sensor may be housed in a sensor body, which may for example be located at the branch point. In this way the main lead as well as the two anchors may be coupled to the sensor body. Advantageously, the sensor may be encapsulated within the sensor body, for example via a separate encapsulation surrounded by a wall of the body, or by an encapsulation that also forms the sensor body. The encapsulation of the sensor can serve to minimise the risk of exposure of the body to parts of the sensor that may be toxic and/or may react with body fluids, such as by corrosion. The encapsulation may use a material suitable for implantation within the body, such as medical grade silicone, polyethylene or stainless steel. In example embodiments the encapsulation encloses the sensor as well as electrical connections associated with the sensor and/or with the pacemaker electrodes (where present), such as an electrical circuit for connecting the sensor and/or with the pacemaker electrodes (where present) to electrical pathways through the main lead. The sensor body may provide for mechanical as well as electrical connectivity between the main lead, the sensor, and (where present) pacemaker electrodes. The sensor body may be insulating in order to avoid any electrical connection between pacemaker electrodes (where present).

It is preferred to have only relatively short distance between the branch point and the anchors, for example each anchor may be joined to the branch point by a straight wire of 3-8 mm in length. Where a sensor body is used then the anchors may be joined to the sensor body by a straight wire of 3-8 mm in length. As will be appreciated from the discussion above, these straight wires may optionally include pacemaker electrodes.

The anchors may have a form similar to anchors of known temporary pacemaker leads. Thus, the anchors may be helical, pigtail or zig-zag wires. The anchors may comprise a wire made of an elastic material having a non-straight shape that will deform toward a straight shape when sufficient tension is applied to the anchor. This requirement can be provided by the pigtail or zig-zag wire. The non-straight shape retains the anchor in the myocardium when no large forces are applied. When it is desired to remove the anchor then tension is applied to straighten it out and allow it to be removed.

Whilst two anchors are described, it will be understood that similar benefits in terms of the stability of the position of the sensor could be obtained by the use of more than two anchors. Thus, the apparatus may include more than two anchors. Additional anchors would require more steps during implantation of the heart anchor lead, but could allow for the sensor body to be located in some regions on the surface of the heart where there might be difficulties in stable placement with fewer anchors, for example regions with a large curvature and/or regions with a significant range of movement of the heart.

The apparatus may include cardiac needles joined to the first anchor and to the second anchor, such as curved cardiac needles as often used in relation to pacemaker leads. In example embodiments the cardiac needles are arranged to be used to implant the anchors into the tissue of the heart, for example into the myocardium. Thus, the anchors may be implanted in a similar way to implantation of anchors for known pacemaker leads. It will be appreciated that with the use of such cardiac needles then the apparatus would be supplied with the cardiac needles attached to the anchors, but that the cardiac needles may be removed after implantation of the anchors and thus during use to secure the sensor at the heart then the cardiac needles will not be present.

The cardiac needles can have a shape and form similar to cardiac needles used with known pacemaker leads. Thus, the cardiac needles may each be a curved needle with an arc shape of any suitable form for threading through the myocardium. Each cardiac needle may be coupled to the corresponding anchor by a wire or suture. As is known for pacemaker leads the apparatus may be arranged for the cardiac needles to be removed once the anchors are in place. The cardiac needles may for example be surgical stainless steel.

The main lead extends from the branch point, which may be a sensor body as discussed above, to a proximal end of the apparatus. In example embodiments the main lead includes electrical connections for the sensor such as power and data connections. Where the apparatus includes one or two pacemaker electrodes then the main lead may include further electrical connections for the pacemaker electrodes. Thus, in some examples the main lead provides for a six-way connection. The main lead may be coupled to a thorax needle for piercing the chest wall. The thorax needle can be a straight or a curved needle of a type known for use to pierce the chest wall when a pacemaker is implanted. The thorax needle may for example be surgical stainless steel.

In example embodiments the main lead terminates with a connector for forming an electrical connection with an adaptor. For example, the main lead may comprise a plug or socket part for coupling with a corresponding socket or plug part of the adaptor. The electrical connection between the connector and adaptor should provide for electrical connectivity to suit the number of connections of the main lead.

Thus, it may provide for a six-way connection or a higher number of terminals for an apparatus with additional functions. In one example the thorax needle has a removable tip such that the sharp point can be removed from the base of the thorax needle, and in this case the connector may be formed on the base of the thorax needle. Thus, the thorax needle may have a break-off tip or it may include a releasable connection between the base of the thorax needle and the tip, such as a screw fitting or a bayonet fitting. The connector may be formed as conductive rings around the base of the thorax needle, with the adaptor hence including a sequence of conductive terminals for alignment with and electrical connection to the conductive rings.

The main lead may be used for transmission of data and power for the sensor and optionally also for pacing signals sent to the pacemaker electrodes. As noted above there may be one or two pacemaker electrodes, and thus the heart anchor lead has the capability for pacing either via two polarities provided by two electrodes, or pacing via a single active electrode. In the latter case there may be a second pacemaker electrode that is normally inactive but that could be used to provide redundancy in case of failure of the first pacemaker electrode.

Advantageously, the adaptor may be arranged to split the pacemaker signal and the sensor signal. Thus, the adaptor may receive the connector of the main lead as an interface with the pacemaker electrodes and the sensor, with pacemaker signals and sensor signals in two separate input/output leads.

The sensor body may hold the sensor along with a circuit for electrical connections between the main lead, the sensor, and the pacemaker electrodes. The sensor body may be arranged to transmit tensile force from the main lead to the anchors, for example via the straight wires mentioned above, so that the anchors can be withdrawn from the myocardium.

Viewed from a second aspect, the disclosure provides a heart monitoring system comprising a sensor for monitoring motion of the heart, a heart anchor lead as discussed above for securing the sensor at the heart, and a data processing apparatus for receiving data from the sensor.

Thus, in example embodiments, the disclosure extends to a combination of the heart anchor lead and sensor with a data processing apparatus for receiving data from the sensor. This may take the form of a system in use, where the heart anchor lead and sensor are implanted in the body and the main lead extends out of the body to provide data to the data processing apparatus. In this case the heart anchor lead would have the cardiac needles removed. The system may also take the form of a kit of parts ready to be used with a patient, in which case the heart anchor lead will be in the form prior to implantation and hence may have cardiac needles and/or a thorax needle coupled to the anchors and/or to the main lead, and the data processing apparatus may not yet be coupled to the heart anchor lead. The system may include a connector and adaptor as described above, with the connector being provided at a proximal end of the main lead and the adaptor being in communication with the data processing apparatus.

The data processing apparatus may be a computer or similar device. It may include a power supply for providing power to the sensor via the main lead. In examples where the heart anchor lead also includes a pacemaker electrode, then the data processing apparatus may optionally have the function of controlling a pacing signal for the pacemaker electrode. If the data processing apparatus has access to the pacing signal, then this may be used to synchronise measurements of heart motion with the heart rhythm. Alternatively, there may be a separate controller for pacemaking. For example, an external pacemaker may be configured to control a pacing signal for one or more pacemaker electrodes in the heart anchor lead. The system may include an adaptor as discussed above in which the pacemaking signal is split from the sensor signal. The data processing apparatus may receive an ECG signal from the patient and may be arranged to use the ECG signal to synchronise the measurements of heart motion with the heart rhythm.

The data processing apparatus may thus have access to heart motion data and optionally also pacing data and it may be arranged to provide information to an operator relating to this data. The data processing apparatus may record the data, and it may process the data in order to provide improved information to the operator. For example, the sensor may be motion sensor such as a three axis accelerometer and the data processing apparatus may process the data from the motion sensor in order to provide a representation of the movement of the heart. The data processing apparatus may provide outputs relating to heart rate, the magnitude of movement, and so on. It may provide data about heart function as discussed in EP 1458290, for example. Optionally the data processing apparatus may also identify other features of the motion sensor data, such as movements resulting from activities of the patient and/or motion induced by other devices, for example a cardiac assist device. Thus, it may provide data about function of a cardiac assist device as discussed in WO 2014/207225, for example.

The data processing apparatus may have the primary function of obtaining and processing information about the motion of the heart. This may be the only function of the data processing apparatus, with control for any pacemaking being carried out through another device. In other examples the data processing apparatus may also control pacing of the heart. In this case then the data received from the sensor, for example data about motion of the heart, may be used in relation to control of the pacing signal. Thus, there may be a feedback mechanism between the pacing signal and the motion of the heart.

The present disclosure also extends to the use of the apparatus of the first aspect, which may include the use of the apparatus within the heart monitoring system of the second aspect. In addition, methods of implantation of the heart anchor lead are encompassed by this disclosure. Thus, viewed from a further aspect the disclosure provides a method for securing a sensor at the heart, the method comprising using the heart anchor lead of the first aspect. Optionally this method may include implanting the anchors at the heart and thereby securing the sensor at the heart. The sensor may for example be secured at the left ventricle of the heart. In some examples the apparatus includes a connector as discussed above and the method comprises coupling this connector to an adaptor of a data processing apparatus to form a heart monitoring system as discussed above. The connector may be formed as a part of the base of a thorax needle as discussed above, and thus the method may include passing the thorax needle through the chest wall, removing a tip of the thorax needle, and coupling the connector at the base of the thorax needle to an adaptor.

A yet further aspect involves the use of the sensor for monitoring the heart, wherein the sensor is implanted with the heart anchor lead of the first aspect. This method may include receiving data from the sensor and using it to determine information about heart function and/or about other aspects of the patient's health, optionally including the function of other devices such as a cardiac assist device. The method may include using pacemaker electrodes of the apparatus as discussed above. In this case. the method may optionally use data from the sensor in relation to the control of pacing via the pacemaker electrodes.

FIG. 1 shows a heart anchor lead for securing a sensor to the heart, according to an embodiment of the present disclosure. The heart anchor lead of FIG. 1 is intended for securing a sensor to the heart, and in particular can be used to temporarily secure a motion sensor such as an accelerometer at the outside surface of the heart. This sensor can be used to obtain measurements that may be used for information about heart function and/or information about related devices, for example as described in EP 1458290 and WO 2014/207225. The sensor is temporarily implanted at the heart to monitor the patient, for example before, during and/or after a surgical operation, and it is removed from the patient after use. Thus, the sensor may be used to monitor the patient's health in relation to a surgical operation, and then it may be removed after the recovery of the patient has progressed sufficiently.

As seen in FIG. 1, the heart anchor lead has some similar structural features to a temporary pacemaker lead, such as a pacemaker lead of the type shown in WO 97/25099, but it is modified compared to a conventional pacemaker lead by the use of a single main lead 12 and two anchors 14 with correspondingly two curved cardiac needles 16 for implantation of the anchors. The anchor sections branch from the main lead 12 at a branch point 18 in the form of a sensor body 18. The sensor body 18 encloses the sensor, which in this example is an accelerometer. The sensor is encapsulated in a material suitable for implantation into the body, such as a bio-safe plastic material.

The heart anchor lead can advantageously also function as a pacemaker and thus in each branch a pacemaker electrode 20 is provided at the proximal end of the anchor 14. Implantation of the two anchors 14 will hence both secure the sensor body 18 and also implant the pacemaker electrodes 20, and this can be done using the curved cardiac needles 16 in the same way as for a conventional pacemaker lead as described below with reference to FIG. 2. FIG. 1 also shows a straight thorax needle 22 for piercing the chest wall so that the main lead 12 can be passed through the chest wall. Again this can be used in a similar fashion to the corresponding parts of a pacemaker lead. A curved thorax needle could also be used.

Figure 3:
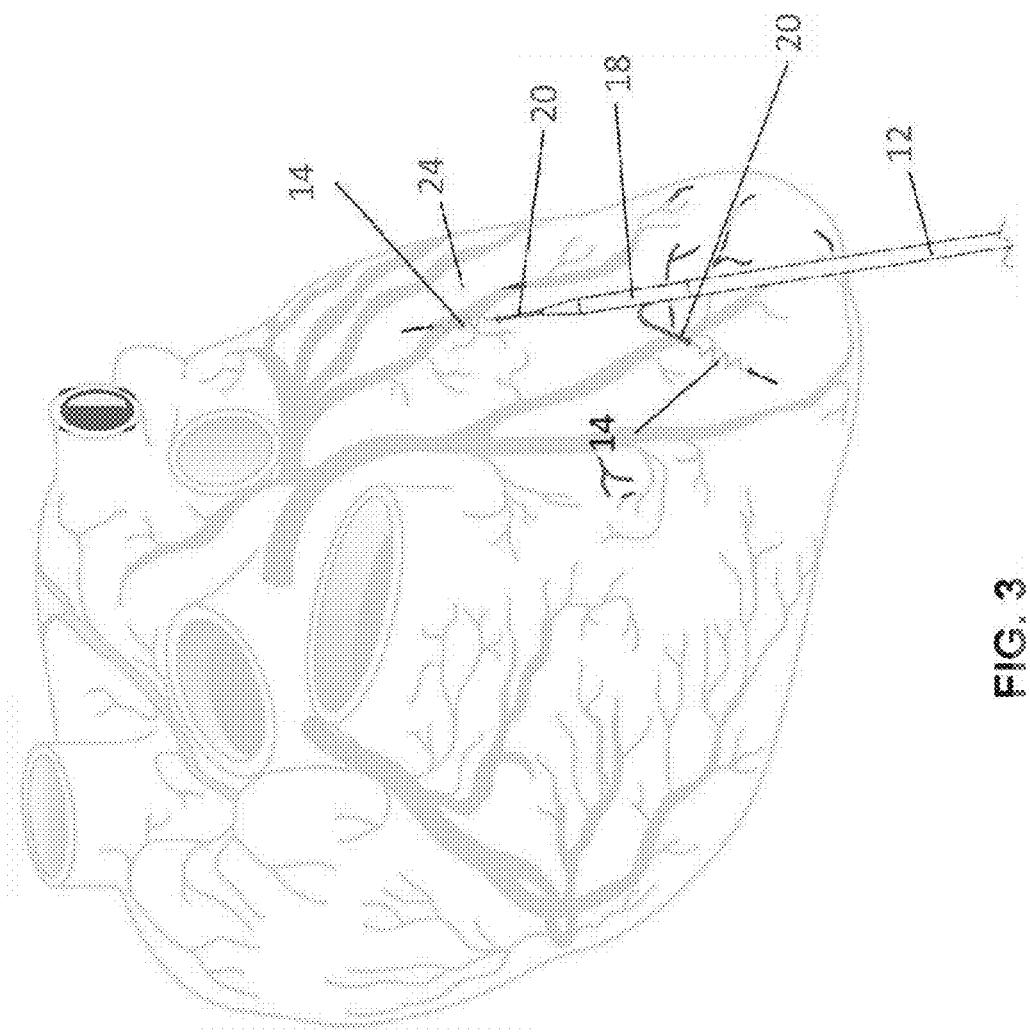
FIG. 3 illustrates an example diagram of the heart anchor lead secured to the heart, according to an embodiment of the present disclosure.

FIG. 2 illustrates an example diagram of an anchor of the heart anchor lead being implanted into the myocardium using a curved needle, according to an embodiment of the present disclosure. In particular, FIG. 2 shows a close up of a section of the myocardium 24 in a location where it is desired to secure the sensor body 18 and implant a pacemaker electrode 20. FIG. 2 shows one branch of the two branches of the heart anchor lead described above in relation to FIG. 1. As is known from implantation of pacemaker leads, the curved cardiac needle 16 is threaded through the tissue of the myocardium 24 and in particular it is passed through the outer part of the myocardium 24 without piercing the heart. The curved cardiac needle 16 is used to pull the anchor 14 into the myocardium 24 so that the pacemaker electrode 20 is brought into conductive contact with the tissue of myocardium 24. As shown in FIG. 1, the pacemaker electrode 20 joins the anchor 14 to the sensor body 18, so this also serves to attach the sensor body 18 to the outer surface of the myocardium 24. When the anchor 14 is in place then the cardiac needle 16 can be removed, typically by simply cutting the wire or suture that joins the cardiac needle 16 to the anchor 14. It will be appreciated that the form of the cardiac needle 16 and the form of the anchor 14 could be varied as desired. In FIGS. 1-3 they are shown as a curved cardiac needle 16 with an arc shape and an anchor 14 formed as a zig-zag wire with a concertina type fold. The cardiac needle 16 may instead have a curve with varying curvature such as that shown in WO 97/25099. The anchor 14 could take the form of a pigtail or spiral rather than a zig-zag.

FIG. 3 illustrates an example diagram of the heart anchor lead secured to the heart, according to an embodiment of the present disclosure. In particular, FIG. 3 shows one configuration for the two anchors 14 after implantation in the myocardium with the sensor body 18 secured in the tissue of the myocardium 24 at the side wall of the heart 26. The sensor body 18 is fixed to the left ventricle. By securing the sensor body 18 and hence the sensor using two anchors 14 then the movement of the sensor is reduced compared to the use of a conventional pacemaker lead with a single anchor 14 as proposed in EP 1458290. The movement of the sensor body 18 relative to the heart 26 is restricted both in terms of unwanted twisting motion along the axis of the main lead 12 and anchor 14 and unwanted sliding of the sensor body 18 across the surface of the heart 26. It will be appreciated that the surgeon can decide the best locations for the two anchors 14, the sensor body 18, and the two pacemaker electrodes 20. The exact placement of the heart anchor lead will depend on the circumstances. However, having multiple anchor points rather than just one anchor point will always improve the stability of the sensor body 18 and hence restrict unwanted motion of the sensor relative to the heart 26. It can also allow for placement of the sensor body 18 in locations on the heart 26 that might be difficult to achieve with only a single anchor 14.

FIG. 3 also shows the main lead 12 extending away from the sensor body 18 and the pacemaker electrodes 20. This lead 12 provides electrical connections to a point outside of the body, and as noted above it can be passed through the chest wall using the straight needle 22. The main lead 12 differs from a conventional pacemaker lead in relation to the number of electrical connections since it is necessary to provide for connection of the sensor (e.g. an accelerometer) as well as two pacemaker electrodes 20. Both data and power are transmitted along the main lead 12. Typically it will provide for a six-way connection between the sensor body 18 and the proximal end of the main lead 12, but it will be appreciate that a greater or smaller number of connections could be used depending on the requirements of the sensor and so on. An electrical circuit may be provided at the distal end of the main lead 12 for interconnection of the main lead with the pacemaker electrodes and the sensor. This electrical circuit may be encapsulated along with the sensor and placed within the sensor body 18.

In additional embodiments, the electrical connections of the main lead 12 can be coupled to an external data processing apparatus such as a computer system (not shown). In particular, FIG. 4 illustrates an example diagram of a connector at a proximal end of the lead, and FIG. 5 illustrates an example diagram of a connector coupled to an adaptor according to embodiments of the present disclosure. In one example, as shown in FIGS. 4 and 5, in order for a suitable electrical coupling to be made outside of the body then the heart anchor lead is arranged with a connector at the base of the straight needle 22 for joining to an adaptor 36 outside of the body. This example uses a simple mechanical coupling to bring electrical terminals 32, 34 at the base of the straight needle 22 into electrical contact with terminals 38 in the adaptor 36. This can allow for a straightforward connection of the sensor body 18 to a data processing apparatus outside of the body without a simple 'snap-fit'. The adaptor 36 may be arranged to split the signals from the sensor from the pacing signals so that a separate controller can be used for pacemaking.

As shown in FIG. 4, the thorax needle 22 in this example is a straight needle 22 and it has a removable tip 28. The sharp tip 28 allows the thorax needle 22 to pierce the chest wall, and the tip 28 can be removed using a releasable connection 30 between the base of the thorax needle 22 and the tip 28. In this example, the releasable connection 30 is shown as a screw thread 30, but it will be appreciated that alternative arrangements may be used, such as a break-off tip 28 or a bayonet fitting. The base of the thorax needle 22 forms an electrical connector with five smaller ring-shaped terminals 32 for data signals including pacemaking signals and the sensor output signals, and one larger ring shaped terminal 34 for carrying a supply voltage. The adaptor 36, which is shown in FIG. 5 joined with the base of the thorax needle 22, has sprung clips 38 for mechanical and electrical connection to the ring-shaped terminals 32, 34 on the base of the thorax needle 22. The adaptor 36 further includes wiring (not shown) for connection to an external data processing apparatus for transmission of control signals and power to the heart anchor lead via the main lead 12, and for receiving sensor data from the sensor held within the sensor body 18.

In a further embodiment, it is desirable to monitor the pumping capacity of a heart during and after cardiac surgery. For example, it may be useful to monitor the pumping capacity of a heart for at least several days after the surgery. Upon the conclusion of the monitoring period, it is further desirable that the sensing device be removed from the heart without the need to re-open the chest cavity for the removal of the sensing device. In the discussion below, an example of the sensing device is an accelerometer, although other alternatives are within the scope of the disclosure.

Figure 6:
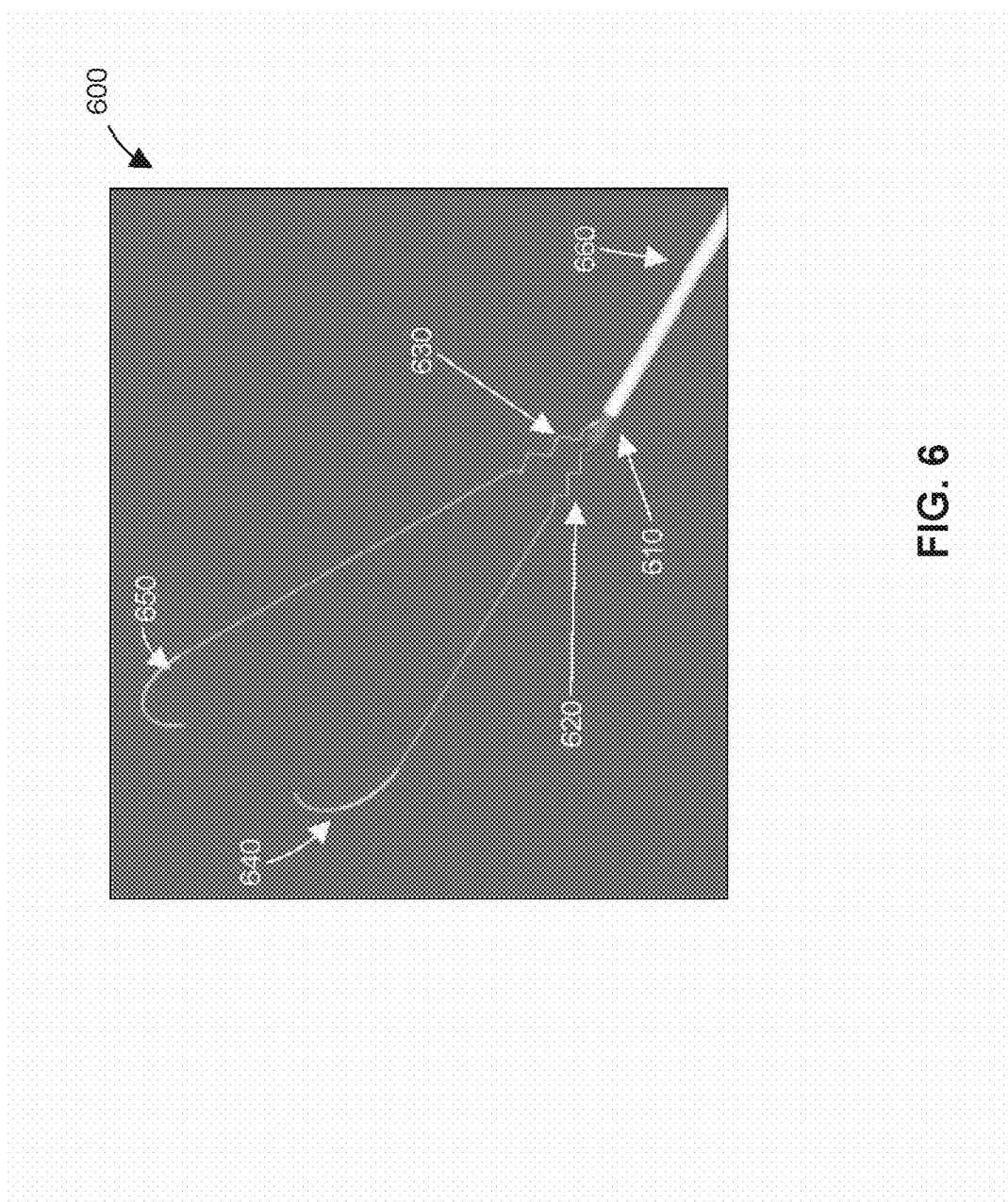
FIG. 6 illustrates an example diagram of a sensing device, according to an embodiment of the present disclosure.

FIG. 6 illustrates an exemplary sensing device 600 that may be used to sense the pumping capacity of a heart. Sensing device 600 includes accelerometer 610, anchors 620 and 630, heart needles 640 and 650, and cable 660. Accelerometer 610 may be a three-dimensional accelerometer configured to acquire motion data of a heart in X, Y, and Z dimensions, so that a full and complete motion data set of the heart may be acquired. In an embodiment, accelerometer 610 is fixed to the left ventricle of the heart. In some embodiments, sensing device 600 may include a gyroscope in addition to or alternative to accelerometer 610 to measure angular velocity and detect heart motion data. As shown in FIG. 6, accelerometer 610 is encapsulated within the body of sensing device 600 to prevent exposure of the heart to sensor parts, and accelerometer 610 is connected to a cable 660. Cable 660 may be an adapter cable and may transmit pace leads and/or sensor data signals to/from sensing device 600. In an embodiment, cable 660 may be flexible and may be made of silicone.

To ensure that the data provided by accelerometer 610 properly captures the pumping capacity of the heart, accelerometer 610 must be stably attached to the heart. In addition, accelerometer 610 needs to maintain a stable position after placement to avoid premature dislodgement, such that accelerometer 610 may acquire accurate motion data from the heart for assessing cardiac function. In an exemplary embodiment, two anchors 620, 630 are provided to ensure no premature dislodgement or disconnection from the heart occurs. In an embodiment, two anchors 620, 630 are placed either side of accelerometer 610, and the angle between the two anchors 620, 630 may be fixed or arbitrary.

The inventors have found that a single anchor is insufficient to ensure stability of accelerometer 610 for the post recovery period during which heart monitoring is desired. For example, sensing device 600 may pivot out from the heart surface when using a single anchor for attachment to the heart surface. A particular challenge is that during the monitoring period, accelerometer 610 must remain stable to ensure valid measurements are provided, while the anchoring arrangement should be such that the sensing device 600 may be removed following the monitoring period without re-opening the chest cavity.

In an exemplary embodiment, anchors 620, 630 use a zig zag approach to anchoring. Attached to the distal end of anchors 620, 630 are heart needles 640, 650 to assist with the initial placement of accelerometer 610. Heart needles 640, 650 may be curved needles, and are used to penetrate the heart surface. Heart needles 640, 650 are removed after placement, such as by cutting off the needles. A further needle (not shown) is a thorax needle, which allows for chest penetration. In certain embodiments, anchors 620, 630 are made of biocompatible stainless steel. Anchors 620, 630 may also function as bipolar pacemaker electrodes in some embodiments.

Figure 7:
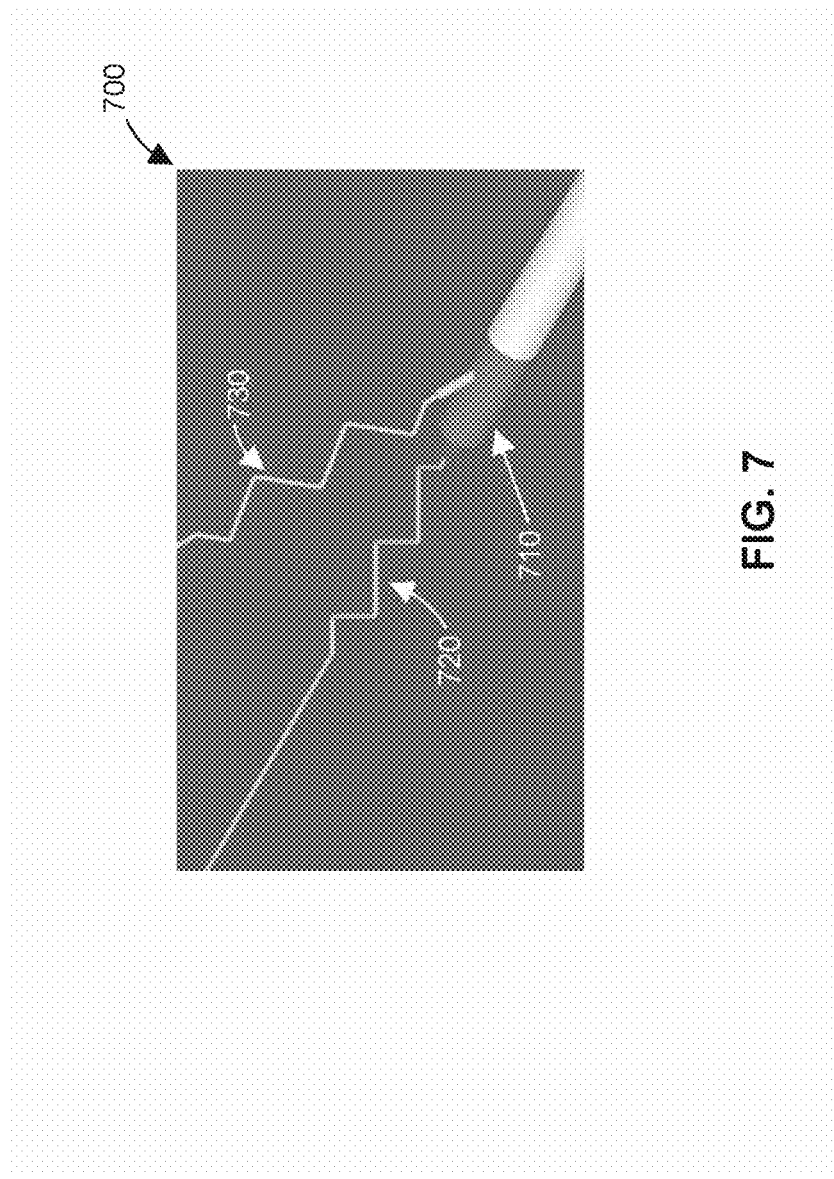
FIG. 7 illustrates an example diagram showing a sensor encapsulation of a sensing device, according to an embodiment of the present disclosure.

FIG. 7 illustrates an example diagram showing a sensor encapsulation of a sensing device 700, according to an embodiment of the present disclosure. Sensing device 700 includes accelerometer 710 and anchors 720 and 730. In some embodiments, sensing device 700, accelerometer 710, and anchors 720 and 730 may be the same as or similar to sensing device 600, accelerometer 610, and anchors 620 and 630, respectively, depicted in FIG. 6. Accelerometer 710 includes an electrical assembly and is encapsulated within the sensor body to prevent exposure of the heart to sensor parts. In an embodiment, accelerometer 610 is fixed to the left ventricle of the heart. In another embodiment, anchors 720 and 730 may be attached to the left and right ventricles of the heart, respectively. Sensing device 700 may acquire motion data of the heart while the chest cavity of a patient is open and/or closed (e.g., open and/or closed thorax). By utilizing two anchors 720 and 730 for attachment of accelerometer 710 to the heart surface, sensing device 700 may provide improved cardiac monitoring of patients undergoing cardiac surgery without unwanted complications, such as the occurrence of abnormal bleeding during placement and removal of the device.

FIGS. 8A, 8B, and 8C illustrate example diagrams of a connector that is configured for placement within a needle, according to an embodiment of the present disclosure. In particular, FIG. 8A illustrates a configuration 800 in which a connector 40 is provided at a proximal end of the main lead 12, and connector 40 is mechanically and/or electrically coupled within a needle 22. In some embodiments, needle 22 may comprise a screw fitting or bayonet fitting for mechanically coupling connector 40 within needle 22. The connector may include any number of electrical terminals 32 for electrical contact within needle 22. FIGS. 8B and 8C illustrate configurations 810 and 820, respectively, in which connector 40 is shown unscrewed or uncoupled from within the needle 22. In some embodiments, main lead 12, needle 22, and electrical terminals 32 of FIGS. 8A, 8B, and 8C may be the same as or similar to main lead 12, needle 22, and electrical terminals 32, respectively, depicted in FIG. 4.

FIGS. 9A, 9B, and 9C illustrate example diagrams of a connector coupled to an adaptor, according to an embodiment of the present disclosure. In particular, FIG. 9A illustrates a configuration 900 in which a connector (e.g., connector 40) is coupled to an adaptor (e.g., adaptor 36). FIG.

9B illustrates configuration 910, which shows the electrical terminals (e.g. electrical terminals 32) of the connector in electrical contact with terminals in the adaptor (e.g., terminals 38). FIG. 9C further illustrates configuration 920, which shows a cross-sectional view of the connector coupled to the adaptor.

FIG. 10 illustrates an example block diagram of an environment 1000 of a sensing device coupled to other components for heart function assessment, according to an embodiment of the present disclosure. In particular, environment 1000 includes an invasive part, a non-invasive part, and accessories and additional equipment for heart function assessment. The invasive part of environment 1000 includes the sensing device (e.g., sensing device 600 or sensing device 700) which is inserted into the chest cavity of a patient and attached to the heart, as described above. The sensing device is coupled to one or more adapter cables, which are included in the non-invasive part of environment 800 (e.g., sterile field). Environment 1000 also includes one or more accessories and additional equipment coupled to the sensing device through one or more adapter cables, and used for data acquisition, data processing, heart monitoring, pace-making, and/or controlling pacing signals. The one or more accessories and additional equipment may include an electronic accessory, an external pacemaker, an ECG machine, and a medical computer with dedicated software for assessing heart function.

Additionally, the present disclosure can be implemented in one or more computer systems capable of carrying out the functionality described herein.

Referring to FIG. 11, an example computer system 1100 useful in implementing the present disclosure is shown. For example, the sensing device (e.g., shown in FIGS. 1-10) may be coupled to a data processing apparatus, such as computer system 1100, for obtaining measurements, analyzing heart motion data and/or pacing data, controlling pacing signals for pacemaker electrodes, synchronizing measurements of heart motion with the heart rhythm, or the like. Various embodiments of the disclosure are described in terms of this example computer system 1100. After reading this description, it will become apparent to one skilled in the relevant art(s) how to implement the disclosure using other computer systems and/or computer architectures.

The computer system 1100 includes one or more processors, such as processor 1104. The processor 1104 is connected to a communication infrastructure 1106 (e.g., a communications bus, crossover bar, or network).

Computer system 1100 can include a display interface 1102 that forwards graphics, text, and other data from the communication infrastructure 1106 (or from a frame buffer not shown) for display on the display unit 1130.

Computer system 1100 also includes a main memory 1108, preferably random access memory (RAM), and can also include a secondary memory 1110. The secondary memory 1110 can include, for example, a hard disk drive 1112 and/or a removable storage drive 1114, representing a floppy disk drive, a magnetic tape drive, an optical disk drive, etc. The removable storage drive 1114 reads from and/or writes to a removable storage unit 1118 in a well-known manner. Removable storage unit 1118, represents a floppy disk, magnetic tape, optical disk, etc. which is read by and written to removable storage drive 1114. As will be appreciated, the removable storage unit 1118 includes a computer usable storage medium having stored therein computer software (e.g., programs or other instructions) and/or data.

In alternative embodiments, secondary memory 1110 can include other similar means for allowing computer software and/or data to be loaded into computer system 1100. Such means can include, for example, a removable storage unit 1122 and an interface 1120. Examples of such can include a program cartridge and cartridge interface (such as that found in video game devices), a removable memory chip (such as an EPROM, or PROM) and associated socket, and other removable storage units 1122 and interfaces 1120 which allow software and data to be transferred from the removable storage unit 1122 to computer system 1100.

Computer system 1100 can also include a communications interface 1124. Communications interface 1124 allows software and data to be transferred between computer system 1100 and external devices. Examples of communications interface 1124 can include a modem, a network interface (such as an Ethernet card), a communications port, a PCMCIA slot and card, etc. Software and data transferred via communications interface 1124 are in the form of signals 1128 which can be electronic, electromagnetic, optical, or other signals capable of being received by communications interface 1124. These signals 1128 are provided to communications interface 1124 via a communications path (i.e., channel) 1126. Communications path 1126 carries signals 1128 and can be implemented using wire or cable, fiber optics, a phone line, a cellular phone link, an RF link, free-space optics, and/or other communications channels.

In this document, the terms "computer program medium" and "computer usable medium" are used to generally refer to media such as removable storage unit 1118, removable storage unit 1122, a hard disk installed in hard disk drive 1112, and signals 1128. These computer program products are means for providing software to computer system 1100. The invention is directed to such computer program products.

Computer programs (also called computer control logic or computer readable program code) are stored in main memory 1108 and/or secondary memory 1110. Computer programs can also be received via communications interface 1124. Such computer programs, when executed, enable the computer system 1100 to implement the present invention as discussed herein. In particular, the computer programs, when executed, enable the processor 1104 to implement the processes of the present invention described above. Accordingly, such computer programs represent controllers of the computer system 1100.

In an embodiment where the invention is implemented using software, the software can be stored in a computer program product and loaded into computer system 1100 using removable storage drive 1114, hard disk drive 1112, interface 1120, or communications interface 1124. The control logic (software), when executed by the processor 1104, causes the processor 1104 to perform the functions of the invention as described herein.

In another embodiment, the invention is implemented primarily in hardware using, for example, hardware components such as application specific integrated circuits (ASICs). Implementation of the hardware state machine so as to perform the functions described herein will be apparent to one skilled in the relevant art(s).

In yet another embodiment, the invention is implemented using a combination of both hardware and software.

It will be apparent to those skilled in the relevant art(s) that various changes in form and detail can be made therein without departing from the spirit and scope of the disclosure. Thus, the disclosure should not be limited by any of the above-described exemplary embodiments, but should be defined only in accordance with the following claims and their equivalents.

What is claimed is:

1. An apparatus for securing a sensor to a heart of a patient, the apparatus comprising:
a heart anchor lead having a main lead;
a sensor included within the main lead, the sensor having a distal end and a proximal end;
a first anchor;
a second anchor configured to attach the sensor to the heart,
a first heart needle coupled to a distal end of the first anchor; and
a second heart needle coupled to a distal end of the second anchor,
wherein the first and second heart needles are configured to implant the first and second anchors, respectively, into heart tissue of the patient.

2. The apparatus of claim 1, wherein the sensor is at least one of an accelerometer configured to detect motion of the heart or a gyroscope configured to measure angular velocity of the heart.

3. The apparatus of claim 1, wherein the first and second anchors are attached to the proximal and distal ends of the sensor by at least one pacemaker electrode.

4. The apparatus of claim 1, wherein the first and second anchors each comprise a wire made of an elastic material, the wire having a non-straight shape that is configured to deform toward a straight shape when sufficient tension is applied to the anchor.

5. The apparatus of claim 1, wherein the main lead is coupled to a thorax needle configured to pierce a chest wall of the patient.

6. The apparatus of claim 1, wherein:
the first anchor is coupled to the distal end or the proximal end of the sensor, and extends outward from the sensor, and
the second anchor is coupled to the proximal end or the distal end of the sensor, and extends outward from the sensor in a direction that forms an angle with the first anchor.

7. The apparatus of claim 1, wherein:
the first anchor is coupled to a first side of the sensor and extends outward from the first side of the sensor, and
the second anchor is coupled to an opposing side to the first side of the sensor and extends outward from the opposing side of the sensor in a direction that forms an angle with the first anchor.

8. The apparatus of claim 1, wherein:
the first anchor is coupled to the proximal end or the distal end of the sensor and extends outward from the sensor, and
the second anchor is coupled to a first side of the sensor and extends outward from the first side of the sensor in a direction that forms an angle with the first anchor.

9. A heart monitoring system for monitoring a patient's heart, the heart monitoring system comprising:
a sensing device comprising:
a heart anchor lead having a main lead, wherein the main lead of the sensing device is coupled to a thorax needle configured to pierce a chest wall of a patient;
a sensor included within the main lead, the sensor having a distal end and a proximal end; and
a first anchor; and
a second anchor configured to attach the sensor to the heart, and
a data processing apparatus coupled to the sensing device and configured to receive motion sensor data from the sensing device.

10. The heart monitoring system of claim 9, wherein the sensing device further comprises a connector at the proximal end of the main lead, wherein the connector is configured to form an electrical connection with an adaptor in communication with the data processing apparatus.

11. The heart monitoring system of claim 9, further comprising an external pacemaker separate from the data processing apparatus, wherein the sensing device further comprises at least one pacemaker electrode, and wherein the external pacemaker is configured to control a pacing signal for the at least one pacemaker electrode.

12. The heart monitoring system of claim 9, wherein the sensing device further comprises at least one pacemaker electrode, and wherein the data processing apparatus is further configured to control a pacing signal for the at least one pacemaker electrode.

13. The heart monitoring system of claim 9, wherein the data processing apparatus is further configured to:
access heart motion data and pacing data; and
provide information based on the heart motion data and pacing data to an operator.

14. The heart monitoring system of claim 9, wherein the data processing apparatus is further configured to identify features of the motion sensor data, including movements resulting from activities of the patient and motion induced by other devices.

15. The heart monitoring system of claim 9, wherein:
the first anchor is coupled to the distal end of the sensor and extends outward from the distal end of the sensor, and
the second anchor is coupled to the proximal end of the sensor and extends outward from the proximal end of the sensor in a direction that forms an angle with the first anchor.

16. The heart monitoring system of claim 9, wherein:
the first anchor is coupled to a first side of the sensor and extends outward from the first side of the sensor, and
the second anchor is coupled to an opposing side to the first side of the sensor and extends outward from the opposing side of the sensor in a direction that forms an angle with the first anchor.

17. The heart monitoring system of claim 9, wherein:
the first anchor is coupled to the proximal end or the distal end of the sensor and extends outward from the sensor, and
the second anchor is coupled to a first side of the sensor and extends outward from the first side of the sensor in a direction that forms an angle with the first anchor.

18. An apparatus comprising:
a heart anchor lead having a main lead;
a sensor included within the main lead, the sensor having a distal end and a proximal end;
a first anchor; and
a second anchor configured to attach the sensor to a heart of a patient;
wherein the first and second anchors are attached to the proximal and distal ends of the sensor by at least one pacemaker electrode.

* * * * *